US006234366B1

United States Patent
Fuchs

(10) Patent No.: US 6,234,366 B1
(45) Date of Patent: May 22, 2001

(54) DISCHARGE CONTROL FOR A MEDIA DISPENSER

(75) Inventor: Karl-Heinz Fuchs, Radolfzell (DE)

(73) Assignee: Ing. Erich Pfeiffer GmbH, Radolfzell (DE)

(*) Notice: Subject to any disclaimer, the term of this patent is extended or adjusted under 35 U.S.C. 154(b) by 0 days.

(21) Appl. No.: 09/255,100

(22) Filed: Feb. 22, 1999

(30) Foreign Application Priority Data

Feb. 25, 1998 (DE) .............................................. 198 07 921

(51) Int. Cl.[7] .............................. A61M 11/00; G08B 3/00

(52) U.S. Cl. ....................................... 222/642; 222/153.13

(58) Field of Search ..................................... 222/642, 644, 222/645, 646, 649, 153.13

(56) References Cited

U.S. PATENT DOCUMENTS 3,669,312 6/1972 Kuckens et al. ....................... 220/70
4,034,757 * 7/1977 Glover .
4,367,955 1/1983 Ballew .................................. 368/10
4,382,688 5/1983 Machamer ............................ 368/10
4,817,822 * 4/1989 Rand et al. .
4,934,358 * 6/1990 Nilsson et al. .
5,020,527 * 6/1991 Dessertine .
5,284,133 * 2/1994 Burns et al. .
5,518,375 5/1996 Vandromme et al. ............ 417/413.1
5,724,957 * 3/1998 Rusbmen et al. .
5,809,997 * 9/1998 Wolf .

FOREIGN PATENT DOCUMENTS 37 38 184 11/1987 (DE) .
40 27 670 8/1990 (DE) .
41 10 302 3/1991 (DE) .
692 20 367 12/1992 (DE) .
44 41 263 11/1994 (DE) .
196 06 703 2/1996 (DE) .
196 10 457 3/1996 (DE) .
196 22 124 * 6/1996 (DE) .
039 004 A2 11/1981 (EP) .

OTHER PUBLICATIONS

German Search Report dated May 17, 1999 for 198 07 921.4.

* cited by examiner

*Primary Examiner*—Kenneth Bomberg
(74) *Attorney, Agent, or Firm*—Quarles & Brady LLP

(57) ABSTRACT

A medium dispenser (2) includes an electric drive (30) and a mechanical lock (23) which is operated by the electrical drive (30) in response to a timed schedule stored in a memory device (36). The electric drive (30) and associated parts may be removably inserted into the medium storage portion of the unit (1). An indicator (40) is provided to signal the user through a visible or audible signal, or both, when the dispenser (1) is available for dispensing operations.

26 Claims, 5 Drawing Sheets

FIG. 3
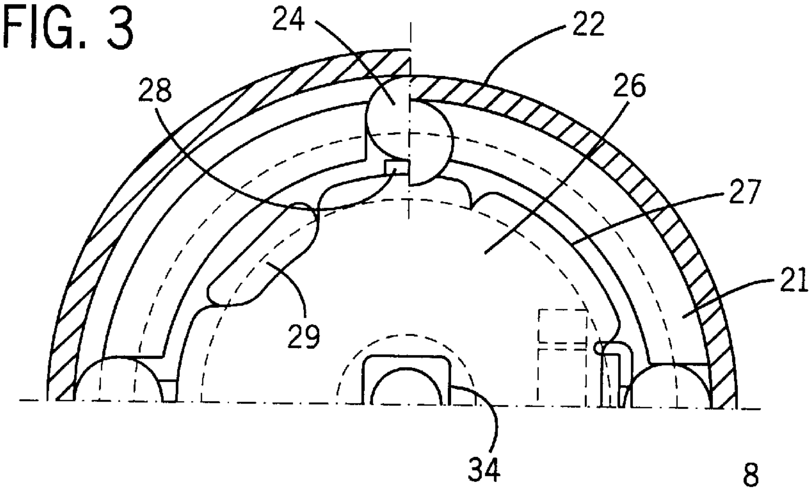
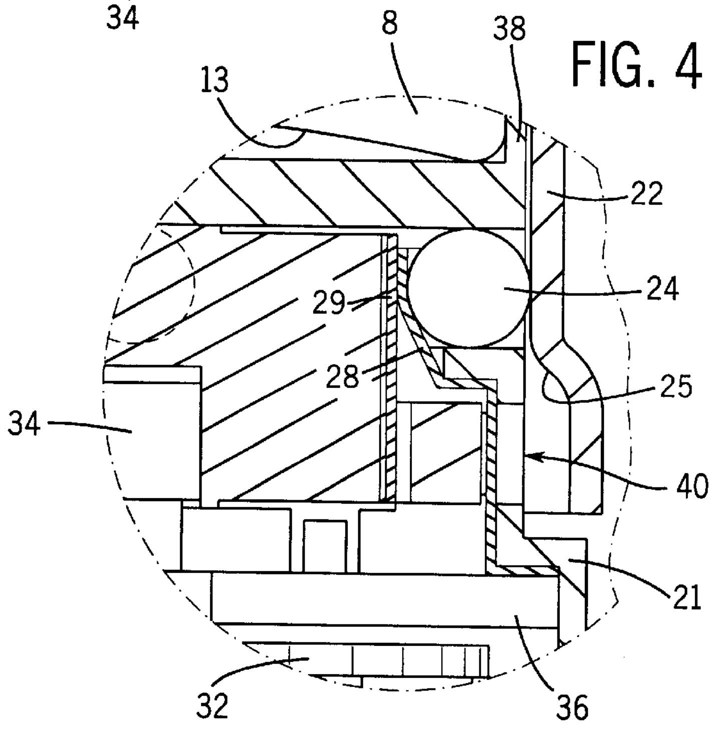
FIG. 4
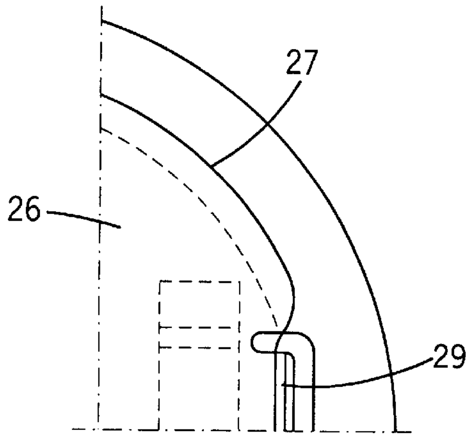
FIG. 5
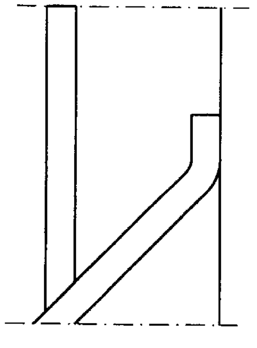
FIG. 6

FIG. 12
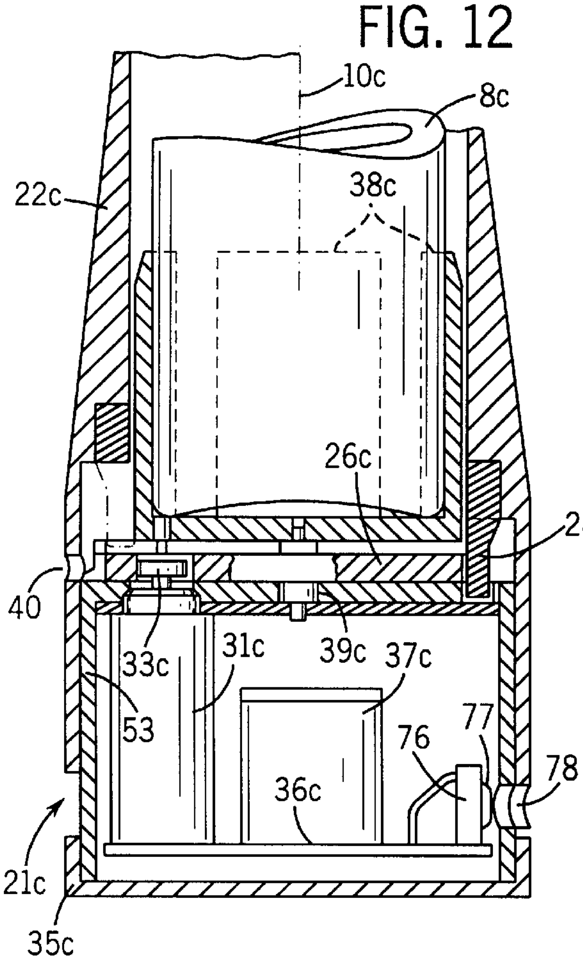
FIG. 13
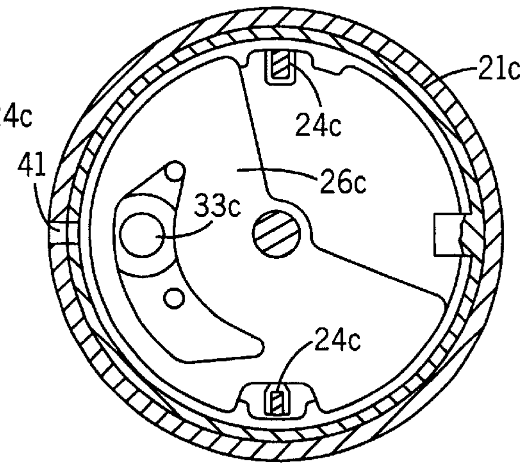
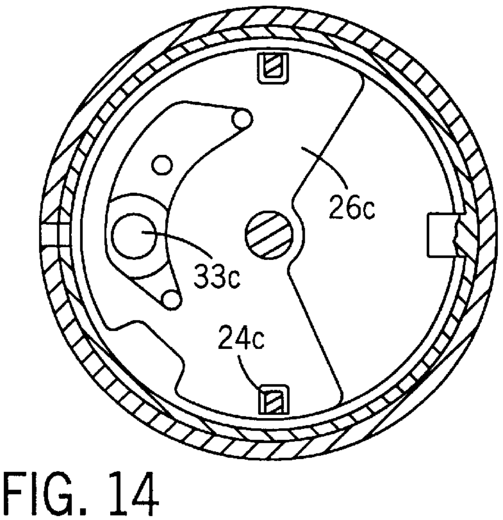
FIG. 14
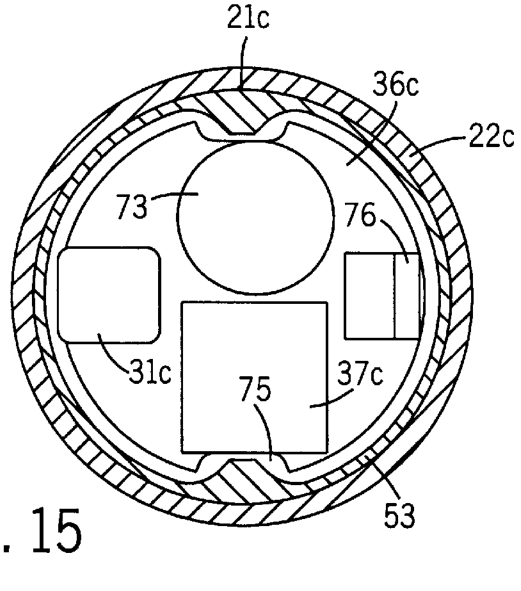
FIG. 15

DISCHARGE CONTROL FOR A MEDIA DISPENSER

TECHNICAL FIELD AND BACKGROUND OF THE INVENTION

The invention relates to a control for controlling the discharge of media from a dispenser. Such dispensers permit operation or actuation with one hand, for example, by a stroke for opening a valve, or by a pumping action. Such dispensers may be gripped or actuated single-handedly. Thereby two fingers of the hand press against remote end faces to squeeze the upper and lower ends of the dispenser towards each other and actuate the control. A return spring, then returns the control of the dispenser from the actuated end position to the initial or rest position. The dispenser may also be constructed for a single dose usage in which it is unnecessary to return the dispenser to the initial or rest position.

Numerous media, such as pharmaceutical media, need to be administered only at specific points in time, in given regular or irregular periods on the basis of special variables, such as medical body values or the like. Strictly maintaining this schedule is achievable only by few people, as experience shows, especially when their capabilities are reduced by illness.

OBJECTS OF THE INVENTION

An object of the invention is to provide an apparatus with which disadvantages of known dispenser controls are avoided or advantageous effects as explained below are achieved. Another object of the invention is to substantially automatically define the points in time of medium discharge or periods during which no medium is to be discharged. A still further object is to configure the control simply or to make it applicable to already existing dispensers.

SUMMARY OF THE INVENTION

According to the invention the control comprises a switching device which is actuated by a timed control signal, such as a pacing circuit, for actuating a dispenser lock, and for actuating an indicator, such as an audible or mechanical warning signal. Thus, the person using or carrying the dispenser is alerted, i.e., that the medium is to be discharged or that no medium is to be discharged. The control is suitable both for solid objects such as pills or the like, and for fluid media which may be liquid, gaseous, powdered and/or pasty. The medium may contain opiates such as morphine for oral or nasal administration.

The control could be actuated from a unit separate from the dispenser by receiving a signal. Otherwise it forms a unit with the dispenser in its operating state, thus disabling and enabling repeated opening or actuation. In this enabling or release action, however, the control may still disable discharge by conveying the medium only within and not out of the dispenser when actuated. For this, a valve is actuated by the control. The signal generator for the signal may be included within the control unit or located remotely therefrom, for example, when a telecontrol signal is employed.

For being transferred to the various indicator or working postures a drive such as a rotary or linear motor is provided within the control unit. The energy storage element is suitably a spring, such as a coil spring, a battery, such as a button-type cell, a rechargeable battery or the like.

The catch or locking member may be fully rotatable, pivotable and/or linearly displaceable. Thereby this member is movable in one direction only or is reversible, the same applying also to all other moving parts, for example an indicator, a counter and the like. The travel from one disabling or locking position to the next is in each case only a portion of travel possible as a whole.

A mechanical or electronic storage device, namely an integrated circuit, such as a chip, is provided as the information storage for emitting a signal. This data storage is replaceable or removable from the control unit at least in part for programming. The, storage unit has two or more connecting contacts for entering the digital program. The contacts are accessible for connecting a programming appliance when the storage is totally encapsulated or located within the control or dispenser.

The control may serve for adjusting or altering the actuating stroke of the dispenser. Thus the dispensers stop-limited stroke length can be varied. For example, several unidirectional substrokes may follow in direct sequence. Each substroke is only permitted after unlocking by the control. Also, the energy storage device driving the control, may be chargeable from the outside, while still being located inside the locking unit. Charging can be mechanical and/or electrical or as a result of the energy manually exerted by the actuating stroke.

A counter or some other sensing means can be provided for sensing the medium dosages discharged from the dispenser and indicating their number to be visible from without. These means may be separate from the control unit or thereon. In the first case, the display is readable on an actuating cap having the medium outlet or is actuated by a mechanical step-by-step system located within the actuating cap. In another case, the control drive may also drive the counting means. Thus, to distinguish a signaled, but missed discharge, this event is either not sensed or is displayed differently than an actual medium discharge. The electronic storage may store these data for later recall.

The control has a support or protective housing for the dispenser so that the latter may be replaced after emptying. The housing comprises two telescopically nested housing parts or caps. Only one of them has a passage through which the head juts outside, which has the medium outlet. Only one housing part accommodates the volumetric majority of the control elements of the control means. The other housing part almost entirely receives the dispenser unit and, at the most, the locking device. Commonly with the medium outlet and a medium impeller this housing part is displaceable relative to a medium reservoir or a pressure space and that housing part which houses the control means. The locking members may be provided directly on the dispenser. They act directly on the two housing parts. If the control unit is entirely removed from the dispenser after opening, the latter may nevertheless be directly manually actuated in the way described for discharging the media.

BRIEF DESCRIPTION OF THE DRAWINGS

Example of embodiments of the invention are explained in more detail in the following description and illustrated in the drawings, which form a part here of and in which:

FIG. 3 is a cross-sectional view through the dispenser of FIG. 2, FIG. 4 is an enlarged detail from FIG. 2, FIG. 5 is the detail of FIG. 4 in plan view, FIG. 6 is a further detail of FIG. 4 in plan view, FIG. 12 is a further embodiment in a view like FIG. 2, FIG. 13 is a cross-section directly above the locking member in FIG. 12 , FIG. 14 section like FIG. 13, but in the locked position, and FIG. 15 is a cross-section below the electronic storage in FIG. 12.

DETAILED DESCRIPTION OF THE PREFERRED EMBODIMENTS

Figure 1:
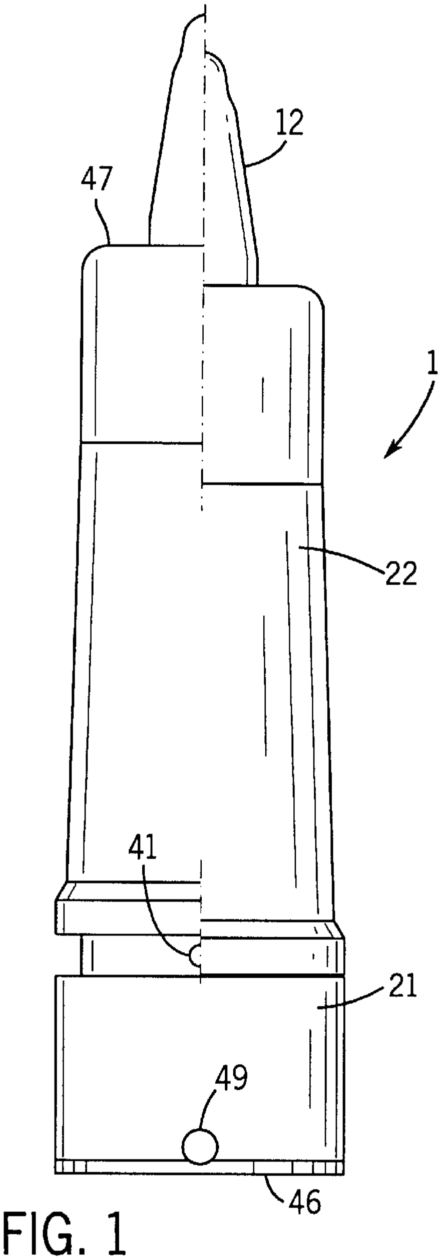
FIG. 1 shows the dispenser of the invention in a rest position and in an actuated end position.

Unit 1 of FIGS. 1–15 provides a control unit which may also serve other purposes, e.g. as the outer housing for a dispenser 2. Each unit 1, 2 has two subunits 3, 4 and 5, 6 which are manually mutually movable synchronously via an axial actuating stroke. Units 3, 5 and units 4,6 are fixedly connected to each other axially and/or rotatively about the center axis 10, but releasable from each other without destruction. Unit 5 of dispenser 2 has a base body 7 fixedly connected to unit 3. Base body 7 has a bottle-shaped reservoir 8 and a housing of a pressure space or a pump. This, housing protrudes into reservoir 8.

Figure 11:
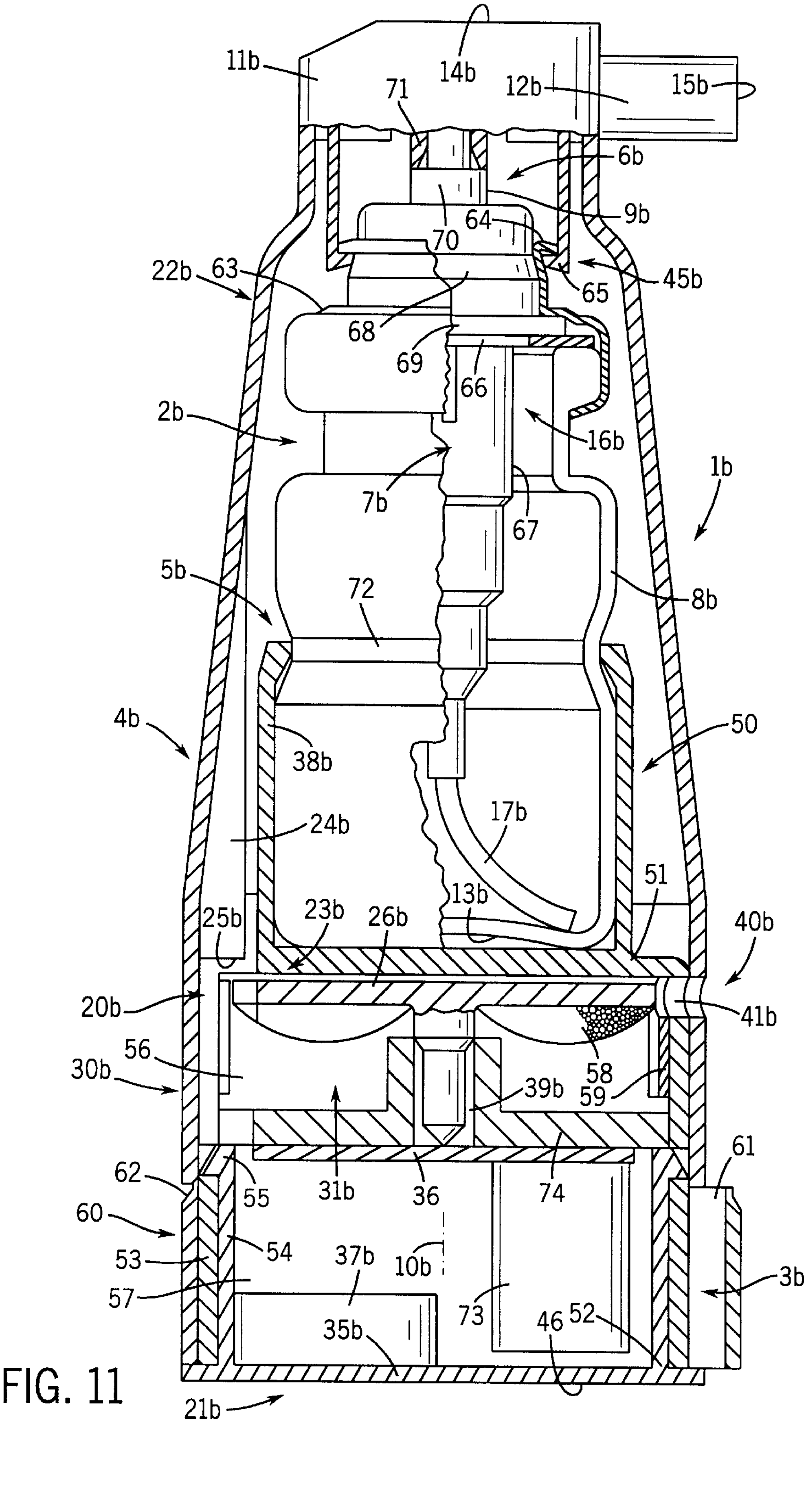
FIG. 11 is a further embodiment in a view like FIG. 2.

Unit 6 of dispenser 2 has a piston unit 9 fixedly connected to unit 4. Axial movement of unit 9 volumetrically varies the pumping space. The piston shaft protrudes out of the pump housing and is fixedly connected to a discharge head 11. Head 11 clasp the reservoir neck by a cap. A stud 12 of head 11 has a reduced diameter protrudes out of the end of unit 4. The bottom of reservoir 5 forms the one handle 13. The cap shoulder of the head cap surrounds stud 12 end forms the other handle 14. The medium outlet 15 is located at the free end of stud 12 in axis 10. Outlet 15 issues directly into the environment. As shown in FIG. 11 the outlet may also be radially oriented relative to axis 10. Outlet 15 may be an atomizing nozzle or a droplet dispenser. Stud 12 of FIG. 1 is suitable for nasal administration. FIG. 11 shows design for oral administration.

The discharge conveyor is a pump 16, such as a thrust piston pump. Reference is made to U.S. Pat. No. 5,884,819, issued Mar. 23, 1999, and U.S. Pat. No. 5,927,559, issued Jul. 27, 1999, for describing further features and effects of these pumps in the present invention. A riser tube 17 juts from the inner end of the pump housing and extends up to the bottom of reservoir 8. On the return stroke of pump 16 medium is sucked from reservoir 8 into the pump chamber through tube 17 and a then, opening inlet valve 18. On the actuating stroke the medium is thus delivered precisely dosed from the pump chamber through an outlet valve 19 and an outlet duct to outlet 15 where it emerges into the environment. Both mutually movable valve elements of valve 19 are provided on unit 9.

Unit 1 comprises an interval switching device 20 or circuit which enables the actuating stroke only at specific points in time and otherwise disables it. A return to the locking position can only occur when an actuating stroke has occurred or, irrespective thereof, after a predetermined time period of release. Unit 3 is partially enclosed by housing 21 and unit 4 is partially enclosed by a housing 22. The housings 21, 22 may accommodate dispenser 2 so that it is located entirely in housing 22 except for the stud 12 which freely protrudes. Units 3, 4 may be positively locked against actuation by a lock 23 irrespective of whether the dispenser 2 is arranged in unit 1 or not. Lock or catch 23 has locking members 24 acting directly on housings 21, 22, namely four balls distributed about axis 10. Balls 24 are mounted in pockets in an end face of housing 21 to be displaceable transverse to axis 10 and prevented from rolling about axis 10. At the inner circumference of the corresponding end, the shell of housing 22 forms an annular locking shoulder 25 which is engaged by the balls 24 when locked. Upon release of the lock 23 and upon actuation, the balls 24 are moved radially inwards counter to the spring stress provided by faces 25 so that they run preloaded on the inner circumference of the adjoining housing shell. For control a locking member 26 is rotatable about axis 10. Member 26 has at the end side or at the circumference a pitch member, namely a cam 27 acting directly on balls 24 directly or via transmission by springs 28, 29. Balls 24 are located radially between faces 25, 27.

Member 26 has the number of protruding locking cams equal to the number of balls 24. Between each couple of cams a release recess is provided into which ball 24 can enter in overcoming the force of the two leaf springs 28, 29. Spring 28 is in one part and directly in contact with balls 24. Spring 28 is non-rotatably located on housing 21 and fixed thereto by axial insertion with a flange shell. Thus its spring end is in preloaded contact with balls 24 at the side remote from the face of shoulder 25. This spring end may also be formed by individual axial and circumferentially interspaced spring tongues. Spring 29 is located between the parts 24, 28 and 26, is rotatable with member 26 and has a spring tongue in each release recess. On translation into the release position this spring tongue 29 is able to directly slide on ball 24 or spring 28, thus enabling ball 24 to be urged radially inwards by the shoulder 25 in overcoming the force of both springs 28, 29. In the locking position only spring 28 is effective so that the locking cam directly acts or without spring action.

For repeatedly locking and releasing lock 23 a drive 30 is provided totally within housing 21. Drive 30 is operable with manual energy or by a miniature electric motor 31. A reduction gear 32 is axially directly flanged to the motor housing. The output member 33 of gear 32 is rotatably and directly connected to member 26 via an axial plug coupling 34. The housing of each of the two units 31, 32 as well as both housings in common have an axial length which is smaller than their diametral extent. The coupling member of shaft 33 has a cornered cross-section and may be axially withdrawn from the coupling opening of the member 26 without destruction. Motor 31 is located on that side of gear 32 which is remote from member 26. Thus motor 31 is further from dispenser 2 than member 26. Motor 31 is fixed, but nondestructively releasable to a console 35 by being axially inserted into openings in bracket 35. Console 35 forms simultaneously the end cover of housing 21 remote from dispenser 2. Cover 35 may be axially withdrawn from housing 21 together with drive 30. Drive 30 or member 26 is located totally within housing 21 and in axis 10 or radially thereto.

A member 36 or 37 is provided directly adjacent to or adjoining each end side of the drive housing. Each member 36, 37 may form a plate, an electronic EPROM storage or an energy storage such as a battery or a button-type cell. Member 36 is located between the drive housing and member 26. Member 36 may be radially withdrawn through an opening from housing 21, for example, for changing the battery or for programming the EPROM. For the same purpose member 37 is likewise accessible after cover 35 has been opened.

Unit 3 comprises a body or cup-shaped support 38 directly axial adjoining balls 24. Support 38 may be separate from or in one part with housing 21. Member 38 bounds the pockets for balls 24 with its end wall. Dispenser 2 and reservoir 8 are commonly inserted into the shell of support 38 while being exposed to radial pressure until bottom 13 abuts on the bottom of support 38. The shell of housing 22 slides on the outer circumference of the support shell until its shell end abuts on an outer annular shoulder of housing 21. Thus the actuating stroke is limited solely by units 3,4. In an opening 39 in the bottom of support 38 the member 26 is rotatably mounted by a spigot. For assembly the member 26 is inserted into the housing, with the cover 35 open, until it abuts on the bottom of the support 38. Spring tongues shown in FIG. 6 may permanently press member 26 against the support bottom or balls 24 and may be in one part with one of the springs 28, 29. Thus, the tongues are slidingly supported on member 36 or 26. Spring 29 is inserted into member 26 in the cited assembly direction thereof. Thus, its spring tongues are locked in the openings of member 26 against motion about axis 10. In this position an end wall of spring 29 may abut on that face of member 26 which opposes member 36. The spring tongues may provide skids which jut from this end wall (FIG. 6). Spring 28 is inserted into housing 21 in the same direction until abutting. Then spring 28 is locked with respect to counterdirected motions by member 26 and by clamping between members 21, 36.

Figure 2:
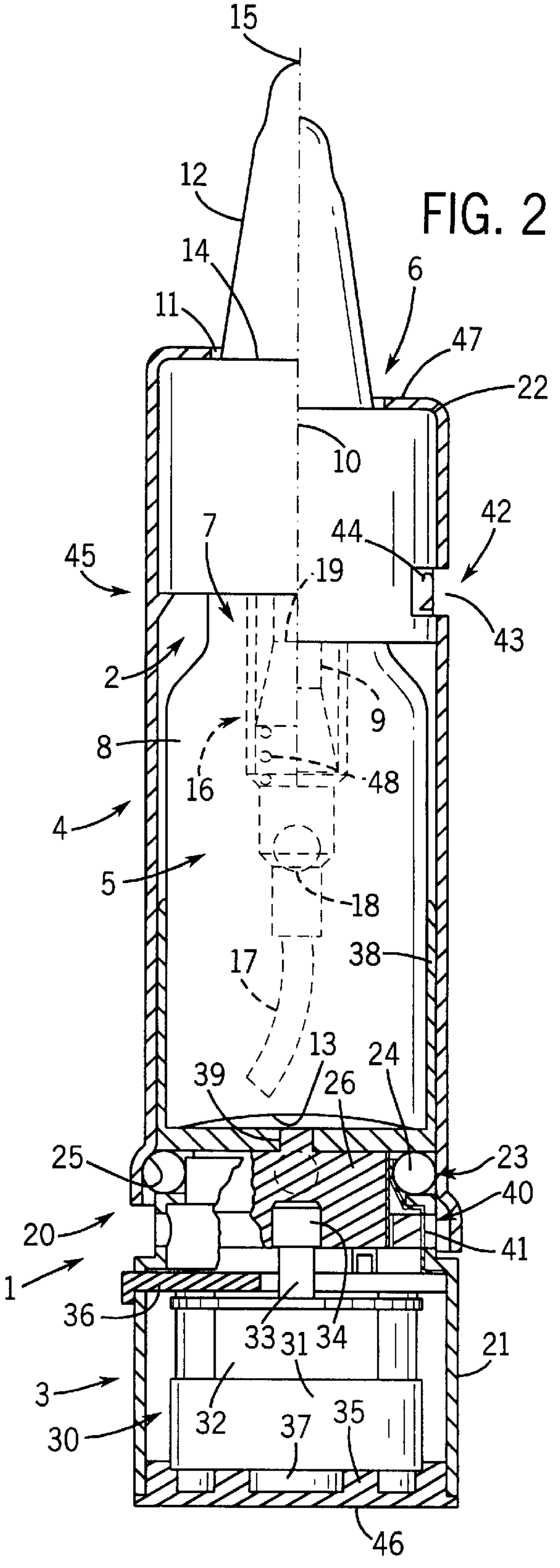
FIG. 2 is an axial section taken through the dispenser of FIG. 1.
Figure 7:
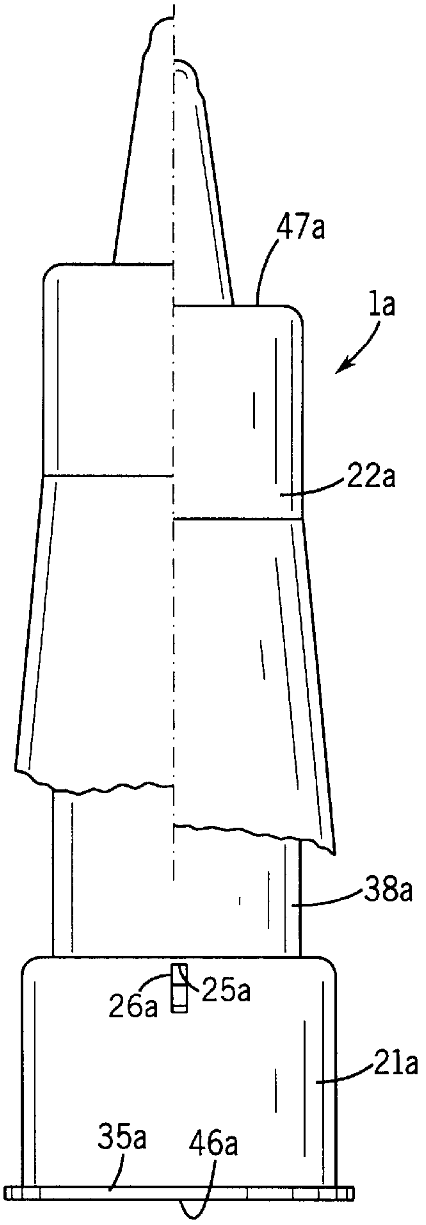
FIG. 7 is a further embodiment in a view like in FIG. 1.
Figure 8:
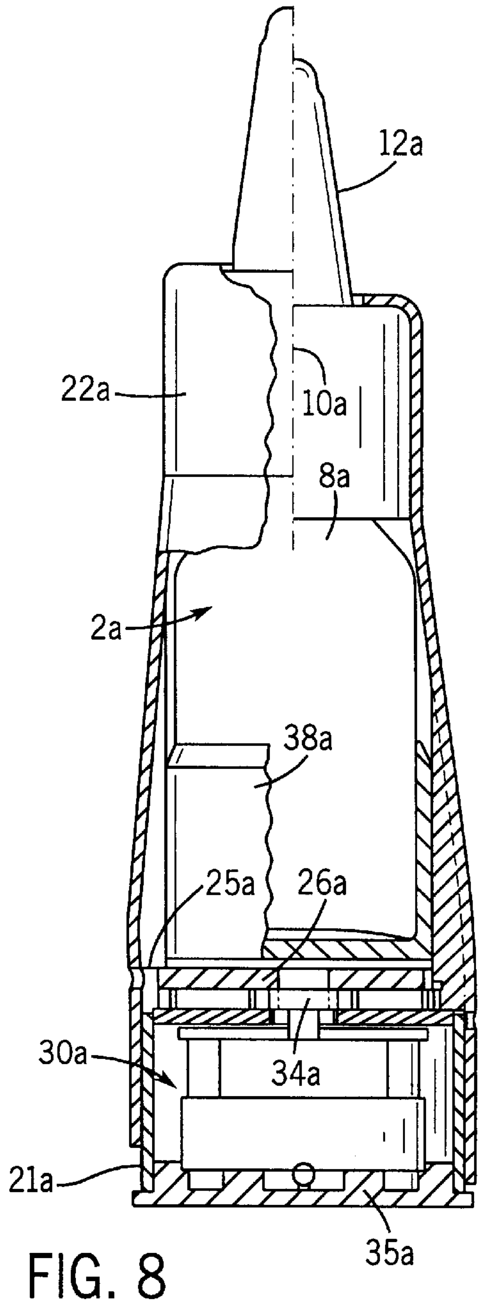
FIG. 8 is an axial section taken through FIG. 7.
Figure 9:
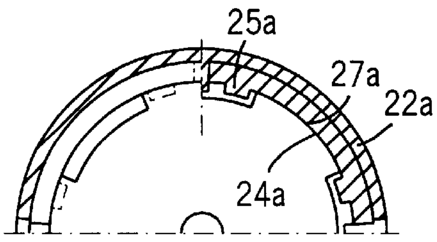
FIG. 9 is a plan view of the opened control of FIG. 8.
Figure 10:
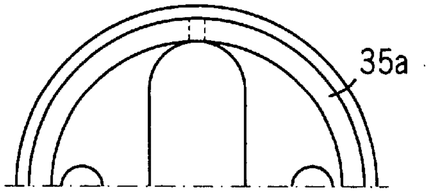
FIG. 10 is view onto the inside of the bottom of the control of FIG. 8.

The locking and release states of control 23 are displayed by an optical indicator 40. The movable indicator member is directly formed by member 26, which has about coupling 34 a flared annular collar with corresponding indicator symbols. These symbols are visible through windows 41 in shell 21 or in spring 28 in the rest position, but are covered from view by the end of shell 22 in the actuated end position. A further indicator 42 for the number of pump strokes executed is provided exclusively on one of units 1,2 and actuated thereby independent of the other unit. In FIG. 2 indicator 42 is provided on dispenser 2, which includes cap 11 having, on its inside, an indicator member including indicating symbols and rotatable about axis 10. The indicator symbols provide a number sequence. only a single symbol is permanently visible through windows 43 in cap 11 and in shell 23.

The cap shell of head 11 engages with radial pressure and axially abuts the shell of housing 22. This shell merges into a stop clasping handle 14. A catch 45 is provided to prevent the head 11 from being pulled out of housing 22 in an upstream direction. This preventing lock may also be a snap connector engaging behind the upstream cap end of the head 11. A similar captive lock could also be provided directly between parts 22, 38 or 22, 21.

The outside of bottom 35 forms handle 46. The flange clasping handle 14 forms handle 47 of the unit 4. With the dispenser 2 inserted there is no direct manual actuating contact with actuators 13, 14, but the same effects occur with actuators 46, 47 as if handles 13, 14 are caused to approach each while the dispenser 2 is apart from unit 1. Thereby a preloaded return spring 48 is further tensioned. This spring is located within the pump housing in the compression space and acts directly on the piston or plunger unit 9. Thus, a separate return spring for units 3, 4 is not needed. After actuation the units 3, 4 are reversed to the rest position by spring 48.

The EPROM 36 may be programmed with a computer by a physician, pharmacist or by the manufacturer so that lock 23 is released only at specific points in a time schedule. For that the program incorporates a time cut-out. Indicator 40 then alerts the user of unit 1,2 as to when he must administer a dosage of the medium and when not. The EPROM 36 is able to memorize these applications whereafter they can be visibly displayed at any given time on the screen of a computer. For programming and polling the EPROM 36 or for charging storage 37 the unit 1 may also comprise an electrical connector 49 accessible from without for a corresponding connector plug. Thus, for this purpose unit I does neither need opening nor removal of the corresponding storage 36, 37. For instance after a pump stroke or at the end of the return stroke units 1, 2 are instantly positively locked against a further pump stroke and indicator 40 shows a red alert in window 41. A time interval for the locking time of, for example 30 seconds, is activated with this locking action. The lock is released at the end of this interval. The release is signaled audibly by an acoustic signal and visibly, by a different color, for instance silver, which is displayed in window 41 until again locking is done. Should a locking not be possible for technical reasons then the locking drive 30 is activated repeatedly in time intervals of 15 seconds and shorter than the locking period. For example three such attempts may be programmed. Should these attempts fail to result in locking, the lock remains open. Whereas, if release is not possible on timeout of the locking period, the drive 30 is activated in the release sense after corresponding time intervals, i.e., without restricting the number of attempts. In FIG. 12 the dispenser also has a switch 76 or contact for priming or initialization. Actuation of switch 76 unlocks units 1,2 instantly and signals a user by an audible signal. Thus, the control is in the original starting or initial state. This state permit a plurality of five pump strokes for priming dispenser 2, namely for filling pump 16 with the medium. Only the next pump stroke is locked by lock 23.

Switch 76 is actuated with a reset key 77, e.g., after insertion of a filled bottle 8 or a complete dispenser 2. For this exchange cap 22 is axially withdrawn from cap 21. The signal may also be given when only a critical number of, for example, ten strokes is still possible after which any further strokes remain locked.

Substantially all components of unit 1 or 2 may be injection molded or formed from plastics. Possibly balls 18, 24, spring 48 and parts of drive or preassembled unit 30 may consist of metal. Instead of balls 24, or additionally, slider tabs may also be provided for locking or unlocking. Motor 31 is driven by energy storage device 37. An electronic control unit closes or opens the power supply via the program of data storage device 36. Data storage device 36 is connected to the control unit via signal leads. The control unit in turn is connected via power leads to the terminals of motor 31 and energy storage device 37.

The configurations as evident from FIGS. 7–15 correspond substantially to those described. Therefore like parts are identified by like reference numerals, having an appended "a", "b" and "c", and all passages of the description apply accordingly for all embodiments. All features of the various embodiments may be incorporated in a sole embodiment. Housing 22*a* of FIGS. 7–10 abuts against bottom 35*a* in the actuated end position. Member 26*a* is an annular plate and no springs are provided. Instead, locking members 24*a* are formed by cams 27*a*. The locking faces 25*a* are formed by the ends of ribs at the inner circumference of housing 22*a*. on the longitudinal edges of these ribs the support shell 38*a* slides radially centered.

In FIG. 11 cap 11*b* is formed in one part with housing 22*b*. Handle 14*b* of both units 1*b*, 2*b* is located at the outermost end of dispenser 2*b*. Stud 12*b* protrudes radially from the outer circumference of cap 11*b* and upstream of handle 14*b*. Outlet 15*b* is oriented radial to axis 10*b*. Handle 14*b* is formed by the outside of the end wall of cap 11*b*. From this wall a sleeve or stud 71 freely protrudes upstream. Shaft 70 of piston unit 9*b* is axially inserted into stud 71 up to abutment while being fixed by a press fit. Stud 71 and cap 11 are formed commonly in one part.

Housing 7*b* of pump 16*b* is secured to the bottleneck by a sleeve or coupling member such as a sheet-metal crimp ring 63, a plastics snap cap or the like. Member 63 forms a stop 64 protruding annularly beyond its outer circumference. A counterstop 65 is provided on parts 11*b*, 12*b* and is in contact with stop 64 in the rest position (FIG. 11). Thus, safety catch 45*b* prevents housing 22*b* from being pulled off from housing 21*b*. Stops 65 are distributed about axis 10*b*, to radially cushion, and are provided on the ends of axial arms which connect to the end wall of cap 11*b* with radial spacing from the inner circumference of the cap shell and in one part.

Housing 7*b* is assembled from two axially interconnecting parts 67, 68. Longer part 67 juts much further into reservoir 8 than shorter part 68 which has within part 67 an appendage jutting into reservoir 8*b* as a closure seat for a vent valve. The movable valve body of this valve is provided on the piston unit 9*b* and closes the valve in the rest position of units 1*b*, 2*b*. The shell of part 67 projects into reservoir 8*b* with a vent outlet or slot opening enveloped by ring 63 and extending up into part 68. Part 68 may be formed in one part with part 67 and is located substantially outside of reservoir 8. Part 68 has a protruding annular flange 69 which is axially tensioned directly against the end face of the reservoir neck with member 63 and with an annular seal 66 interposed.

Ring 63 has a lug or jacket projecting from flange 69 down-stream and closely resting on the outer circumference of part 68. The end of this lug forms stop 64 of catch 45*b* and protrudes radially outwards.

Bottle 8 has a depression 72, in its outer circumference and spaced from its constricted neck and handle 13*b*. Annular constriction 72 or waist is positively engaged by cams of the end of clamps 38*b*. Recess 72 forms at the inner circumference a protuberance so that the wall thickness of bottle 8*b* in this region is roughly equal to that in the other regions.

Locking member 24*b* is contained in stationary housing 22 and is formed as an axial rib 24*b* protruding from the inner circumference of the housing shell. The upstream end of rib 24*b* forms the locking shoulder 25*b* for which a counter member is directly an end face of locking member 26*b*.

The runner or rotor of motor 31*b* is formed by member 26*b* which constitutes the motor armature and carries the motor coil 58 or the armature winding and the coil core. The coil 58 is located at the end side of plate 26*b* remote from member 24*b*. The other end side of plate 26*b* forms the counter face for shoulder 25*b*. Housing 21*b* or a separate housing part 51 forms the stator of motor 31*b* and the housing thereof. Permanent magnets 59 are fixed on the inner circumference of housing 21*b* or 51. Magnets 59 are uniformly distributed about axis lob. No gear is provided between motor 21*b* and member 26*b*. Two separate coils 58 may also be provided. Sliding contact within bearing 39*b* and/or on the circumference of disk 26*b* may supply coil means 58 with electrical power from battery 37*b*.

Motor 31*b* belongs to a unit 50 inserted as pre-assembled module into the lower end of housing 22*b*, from which it may also be withdrawn. Unit 50 has two caps or housing parts 51, 52. The oppositely directed housing shells 53, 54 are fixedly interconnected by a snap connector 55. To the one-part housing 51 belongs support 38*b* and shell 53. Shell 53 protrudes upstream from the support bottom and slidingly rests on the inner circumference of housing 22*b*. Shell 54 belongs to the one-part console 35*b*, is in contact with the inner circumference of shell 52 and comprises at its end the resilient snap members of connector 55. The inner space of housing 51, 52 is subdivided transverse to axis 10 by an intermediate plate 74 into two separate spaces 56, 57. Coil 58 and magnets 59 are located in the downstream space. The EPROM 36, battery 37 and a signal generator 73 for emitting an acoustic signal or the like are located in the upstream space. Plate 74 also forms the stationary bearing body of bearing 39. The movable bearing body or spigot is in one part with member 26*b*. Bearing 39*b* is a radial and axial bearing, whereby the axial forces oriented upstream may directly act on part 36*b*. EEPROM circuit support 36*b* is secured to the upstream end side of plate 74 and may in turn comprise holders to which battery 37*b* and signal generator 73 are secured to be exchangeable irrespective of all other parts.

In FIG. 11 the rest position of the dispenser 2*b* and the release position of switching device 20*b* is shown. In the stroke motion region of member 24*b* a passage opening is provided for element 24*b* on disk 26*b* and, where necessary, on winding 58 as well as on magnet 59 located in this region. A corresponding passage is also provided in disk 74. At the end of the pump stroke the shoulder 25*b* may reach into the region of plate 36*b* where it, as on actuating member, activates a switching action mechanically or without direct contact via a magnetic field. This switching action is used to reverse the action of motor 31*b* in the release sense so that member 26*b* snaps into the locked position at the end of the return stroke. For positively limiting the pump stroke the shoulder 25*b* may abut, for example at the end of shell 54 on which also plate 74 is supported. A passage for member 24 is also provided in the end wall as well as in shell 53 of housing part 51 and directly adjoins the outer circumference of the associated clip 38.

For removal, the unit 50 is to be fully withdrawn downwards from the housing 22*b*. Thereby support 38*b* releases reservoir 8*b* in overcoming a spring force. Thereafter parts 51, 52 may be untied from each other so that parts 36*b*, 37*b*, 73 may be replaced or adjusted. Furthermore, control means may be provided which by actuating a separate handle releases catch 45*b* so that dispenser 2 may be withdrawn downwards from the housing 22 commonly with or after unit 50. Thereby shaft 70 releases from stud 71. A further dispenser 2*b* may then be inserted in the reverse direction and sequence.

Units 1*b*, 2*b* include a tamper-evident closure 60 which only permits use or a pump stroke once a tamper member 61 has been destroyed, displaced or removed. Member 61 is in one part with housing 22*b* namely as a lower extension of the housing shell. The sleeve or member 61 abuts against the end wall of console 35*b*, adjoins by a knockout 62 the housing shell 22*b* and has a length about equal to the length of the pump stroke. On the right in FIG. 11 the member 61 is shown in a state in which it has already been separated from the knockout 62 and lifted off from the outer circumference of shell 53. The pump stroke is unlocked only after member 61 is fully unwound. The first pump stroke then starts the electronics of the switching device 20*b*. Drive 30*b* requires very little power due to the disclosed constructions. Window 41*b* also traverses housing shell 22*b*.

In FIGS. 12 to 15 the locking member 24*c* is exchangeable on housing 22*c*. By selecting members 24*c* of varying length the stroke of units 1*c*, 2*c* may be altered. The output member 22*c* is a friction wheel or gear wheel which drivingly engages a counter face of member 26*c*. This counter face is concavely curved about axis 10*c* can be formed by an opening which is circumferentially and uninterruptedly bounded. The ends of this opening form stops for the locking and release position. The rotation direction motor 31*c* is thus reversed for locking and releasing. Motor 31*c*, battery 37*c* and switch 76 stand on plate 36*c* directly juxtaposed with console 35. Motor 31 carries plate 36*c* with the remaining components being arranged thereon solely by the other motor end being fixed to the bottom of housing 21. Member 26*c* is located between this bottom and the bottom of support 38*c*.

Member 26*c* extends only over part of a full circle, namely over more than 180°. Member 26*c* has at its outer circumference a recess for one of the two locking members 24*c*. When released the other member 24*c* is located besides member 26*c* (FIG. 13). Plate 36*c* could directly positively engage housing 21*c* for preventing rotation with a lock 75. Lock 75 has circumferential cutouts in plate 36*c* and internal circumferential cams on housing 21*c*.

Switch key 77 is accessible through a window 78 in shell 53 or in housing 22*c* by means of a pin or the like.

It will be appreciated that the cited features, such as properties, effects, configurations etc. may be provided precisely as described, or merely substantially or approximately so and may also greatly deviate therefrom depending on the particular requirements.

What is claimed is:

1. A control for controlling discharge of a medium from a dispenser having a housing with an upper cylindrical portion that is moved axially with respect to a lower cylindrical portion in operating the dispenser to discharge a dose of medium from the dispenser, the control comprising:

a switching device actuated by a timed control signal to enable discharge of medium from the dispenser, and a control member preventing discharge of said medium until said control member is moved in response to said switching device being actuated; and wherein said control member is a rotor which is disposed with said switching device in said lower cylindrical portion of said housing, said control member being rotatable around a rotor axis that is aligned with a longitudinal axis of said housing.

2. The control according to claim 1 and further including a lock for releasably locking the dispenser against being actuated, wherein said switching device actuates said lock.

3. The control according to claim 2, wherein said lock includes a locking member which further includes said control member.

4. The control member of claim 3, wherein the locking member acts solely on at least one of the upper cylindrical portion and the lower cylindrical portion of the housing to prevent a discharge operation of the dispenser.

5. The control according to claim 2, wherein said lock is disposed around a portion of a periphery of said control member.

6. The control according to claim 2, wherein said control provides a preassembled unit separate from the dispenser and including a housing for receiving the dispenser.

7. The control according to claim 1, wherein said control rotor includes a control cam.

8. The control according to claim 1, wherein an emitter is included which emits said control signal.

9. The control according to claim 8, wherein said emitter includes a data storage device for electronically storing control data defining a variable control program which controls the timing of the timed signal.

10. The control according to claim 9, wherein said data storage device is separable from said control means substantially without destruction.

11. The control according to claim 1, wherein said switching device further includes a motor disposed in the lower cylindrical portion of the housing for driving said control member.

12. The control according to claim 11, wherein said switching device includes an electromechanical drive for driving said control member.

13. The control according to claim 11, wherein said motor (30) includes a rotational motor defining a circumferential width and an axial extension smaller than said circumferential width.

14. The control according to claim 11, wherein said includes a driving output member directly connected to said control member (26).

15. The control according to claim 11, wherein said motor includes a drive output member, a linear coupling being included and connecting said drive output member with said control member.

16. The control according to claim 11, wherein said motor and said control member are at least one of coaxial and juxtaposed, in said lower cylindrical portion of said housing.

17. The control according to claim 11, wherein said motor includes a stator and a drive output member driven via said stator, said drive output member and said control member commonly providing a preassembled unit.

18. The control according to claim 1, wherein said control member includes a pitch member.

19. The control according to claim 1, whereby the dispenser includes a lowermost bottom, wherein said switching device is operationally located adjacent to the bottom.

20. The control according to claim 1 and further including an energy store (37) which is disposed in said lower cylindrical portion of said housing and which emits energy for operating said switching device.

21. The control according to claim 1, wherein said switching includes an energy storage including an energy output which is electronically controlled.

22. The control according to claim 1 and further including a dispenser support, wherein said dispenser support exchangeably holds the dispenser.

23. The control according to claim 22, wherein said dispenser support movably mounts said control member.

24. The control according to claim 1 and further including an indicator, wherein said control means define control states, said indicator (40, 42), displaying at least one of said control states.

25. The control according to claim 1, the dispenser defines an overall length extension, and wherein said housing and said control are assembled in an assembly for containing a medium reservoir and medium discharge actuator subassembly, and wherein said control internally receives the subassembly over most of an overall length of said housing and control assembly.

26. The control according to claim 1 and further including a control housing, wherein said switching device is located in a control housing, said control housing being assembled from two housing members, at least one of said two housing members including a cup housing.

* * * * *

UNITED STATES PATENT AND TRADEMARK OFFICE

CERTIFICATE OF CORRECTION

PATENT NO. : 6,234,366 B1
DATED : May 22, 2001
INVENTOR(S) : Karl-Heinz Fuchs

It is certified that error appears in the above-identified patent and that said Letters Patent is hereby corrected as shown below:

Column 3,
Lines 33 and 35, “axis 10” should be -- axis 11 --.
Line 35, “outlet 15” should be -- outlet 12 --.

Column 4,
Line 8, “member 36” should be -- member 26 --.

Column 5,
Line 47, “spring 48” should be -- spring 41 --.

Column 7,
Line 42, “lob” should be -- 10b --.

Signed and Sealed this

Twenty-sixth Day of November, 2002

*Attest:*

JAMES E. ROGAN

*Attesting Officer*

*Director of the United States Patent and Trademark Office*